(12) United States Patent
Dale

(10) Patent No.: US 8,771,425 B2
(45) Date of Patent: Jul. 8, 2014

(54) PROCESS FOR THE TREATMENT OF LIGNOCELLULOSIC BIOMASS

(75) Inventor: Bruce E. Dale, Mason, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 13/591,092

(22) Filed: Aug. 21, 2012

(65) Prior Publication Data

US 2012/0325202 A1 Dec. 27, 2012

Related U.S. Application Data

(63) Continuation of application No. 12/226,763, filed as application No. PCT/US2007/010454 on Apr. 30, 2007, now Pat. No. 8,394,611.

(60) Provisional application No. 60/796,375, filed on May 1, 2006.

(51) Int. Cl.
*C08B 30/00* (2006.01)

(52) U.S. Cl.
USPC .......................................................... 127/34

(58) Field of Classification Search
None
See application file for complete search history.

(56) References Cited

U.S. PATENT DOCUMENTS

| | | | |
|---|---|---|---|
| 4,064,276 | A | 12/1977 | Conradsen et al. |
| 4,263,744 | A | 4/1981 | Stoller |
| 4,370,351 | A | 1/1983 | Harper |
| 4,526,791 | A | 7/1985 | Young |
| 4,600,590 | A | 7/1986 | Dale |
| 4,624,805 | A | 11/1986 | Lawhon |
| 4,644,060 | A | 2/1987 | Chou |
| 4,848,026 | A | 7/1989 | Dunn-Coleman |
| 5,037,663 | A | 8/1991 | Dale |
| 5,047,332 | A | 9/1991 | Chahal |
| 5,171,592 | A * | 12/1992 | Holtzapple et al. ............. 426/69 |
| 5,370,999 | A * | 12/1994 | Stuart ............................. 435/99 |
| 5,473,061 | A | 12/1995 | Bredereck et al. |
| 5,736,032 | A | 4/1998 | Cox et al. |
| 5,865,898 | A | 2/1999 | Holtzapple et al. |
| 5,939,544 | A | 8/1999 | Karstens et al. |
| 6,106,888 | A | 8/2000 | Dale et al. |
| 6,176,176 | B1 | 1/2001 | Dale et al. |
| 6,416,621 | B1 | 7/2002 | Karstens |
| 6,444,437 | B1 | 9/2002 | Sporleder et al. |
| 6,524,848 | B2 | 2/2003 | McNelly |
| 7,049,485 | B2 | 5/2006 | Sticklen et al. |
| 7,371,926 | B2 | 5/2008 | Sticklen |
| 7,494,675 | B2 | 2/2009 | Abbas et al. |
| 7,771,565 | B2 | 8/2010 | Kirov et al. |
| 7,910,338 | B2 | 3/2011 | Hennessey et al. |
| 7,915,017 | B2 | 3/2011 | Dale |
| 8,367,378 | B2 | 2/2013 | Balan et al. |
| 2003/0044951 | A1 | 3/2003 | Sporleder et al. |
| 2005/0233423 | A1 | 10/2005 | Berka et al. |
| 2006/0014260 | A1 | 1/2006 | Fan et al. |
| 2006/0130396 | A1 | 6/2006 | Werner |
| 2006/0177917 | A1 | 8/2006 | Warzywoda et al. |
| 2007/0031918 | A1 * | 2/2007 | Dunson et al. ................... 435/41 |
| 2007/0037259 | A1 | 2/2007 | Hennessey et al. |
| 2007/0192900 | A1 | 8/2007 | Sticklen |
| 2007/0202214 | A1 | 8/2007 | Lewis et al. |
| 2007/0227063 | A1 | 10/2007 | Dale et al. |
| 2007/0287795 | A1 | 12/2007 | Huda et al. |
| 2008/0008783 | A1 | 1/2008 | Dale |
| 2008/0229657 | A1 | 9/2008 | Senyk et al. |
| 2008/0256851 | A1 | 10/2008 | Lumb |
| 2008/0280236 | A1 | 11/2008 | Wright |
| 2009/0011474 | A1 | 1/2009 | Balan et al. |
| 2009/0042259 | A1 | 2/2009 | Dale et al. |
| 2009/0053770 | A1 | 2/2009 | Hennessey et al. |
| 2009/0053771 | A1 | 2/2009 | Dale et al. |
| 2009/0061486 | A1 | 3/2009 | Edwards et al. |
| 2009/0093027 | A1 | 4/2009 | Balan et al. |
| 2009/0178671 | A1 | 7/2009 | Ahring |
| 2009/0318670 | A1 | 12/2009 | Dale et al. |
| 2010/0159521 | A1 | 6/2010 | Cirakovic et al. |
| 2010/0267999 | A1 | 10/2010 | Lau et al. |
| 2011/0192559 | A1 | 8/2011 | Venkatesh |
| 2011/0201091 | A1 | 8/2011 | Dale |
| 2011/0300269 | A1 | 12/2011 | Dale et al. |
| 2012/0064574 | A1 | 3/2012 | Tokuyasu et al. |
| 2012/0085505 | A1 | 4/2012 | Sabourin |
| 2012/0125548 | A1 | 5/2012 | Cohen |

(Continued)

FOREIGN PATENT DOCUMENTS

| AU | 200043995 B2 | 11/2000 |
|---|---|---|
| CA | 2573046 A1 | 1/2006 |

(Continued)

OTHER PUBLICATIONS

U.S. Appl. No. 11/729,632, Examiner Interview Summary filed Oct. 30, 2009, 9 pgs.
U.S. Appl. No. 11/729,632, Non Final Office Action mailed May 6, 2009, 4 pgs.
U.S. Appl. No. 11/729,632, Response filed Sep. 11, 2009 to Non Final Office Action mailed May 6, 2009, 9 pgs.
U.S. Appl. No. 11/897,119, Restriction Requirement mailed Sep. 30, 2011, 6 pgs.
U.S. Appl. No. 12/226,763, Non Final Office Action mailed Aug. 22, 2011, 13 pgs.
U.S. Appl. No. 12/229,225, Non Final Office Action mailed Aug. 16, 2011, 6 pgs.
U.S. Appl. No. 12/229,225 Response filed Nov. 15, 2011 to Non Final Office Action mailed Aug. 16, 2011, 12 pgs.

(Continued)

*Primary Examiner* — Qiuwen Mi
(74) *Attorney, Agent, or Firm* — Clark IP Law, PLC

(57) ABSTRACT

A process for the treatment of biomass to render structural carbohydrates more accessible and/or digestible using concentrated ammonium hydroxide with or without anhydrous ammonia addition, is described. The process preferably uses steam to strip ammonia from the biomass for recycling. The process yields of monosaccharides from the structural carbohydrates are good, particularly as measured by the enzymatic hydrolysis of the structural carbohydrates. The monosaccharides are used as animal feeds and energy sources for ethanol production.

25 Claims, 2 Drawing Sheets

(56) References Cited

U.S. PATENT DOCUMENTS

| | | |
|---|---|---|
| 2012/0125551 A1 | 5/2012 | Cohen et al. |
| 2012/0187228 A1 | 7/2012 | Camp et al. |
| 2013/0196398 A1 | 8/2013 | Bals et al. |
| 2013/0217073 A1 | 8/2013 | Chundawat et al. |
| 2013/0280762 A1 | 10/2013 | Dale et al. |

FOREIGN PATENT DOCUMENTS

| | | |
|---|---|---|
| CA | 2610797 A1 | 12/2006 |
| CA | 2752604 A1 | 8/2010 |
| CA | 2 762 985 C | 7/2013 |
| CA | 2 650 860 C | 9/2013 |
| CN | 101223273 A | 7/2008 |
| CN | 102597247 A | 7/2012 |
| DE | 20301645 U1 | 4/2003 |
| EP | 1247781 A2 | 10/2002 |
| EP | 1690944 A1 | 8/2006 |
| IN | 249187 | 10/2011 |
| IN | 9645/DELNP/2011 A | 2/2013 |
| JP | 2008161125 | 7/2008 |
| JP | 2011160753 A | 8/2011 |
| RU | 22157655 C1 | 11/2003 |
| WO | WO-8500133 | 1/1985 |
| WO | 200061858 A1 | 10/2000 |
| WO | 0237981 A2 | 5/2002 |
| WO | 2004/033920 A1 | 4/2004 |
| WO | 2006128304 A1 | 12/2006 |
| WO | 2007005918 A2 | 1/2007 |
| WO | 2007005918 A3 | 1/2007 |
| WO | WO-2007130337 A1 | 11/2007 |
| WO | 2008020901 A2 | 2/2008 |
| WO | 2009/045527 A1 | 4/2009 |
| WO | WO-2010098408 A1 | 9/2010 |
| WO | WO-2010147218 A1 | 12/2010 |
| WO | WO-2011028543 A2 | 3/2011 |
| WO | 2011/133571 A2 | 10/2011 |
| WO | WO-2011133571 A3 | 10/2011 |
| WO | WO-2012012594 A1 | 1/2012 |
| WO | 2012071312 A2 | 5/2012 |
| WO | WO-2012088429 A2 | 6/2012 |
| WO | 2013/106113 A2 | 7/2013 |
| WO | 2013/131015 A1 | 9/2013 |
| WO | 2013/163571 A2 | 10/2013 |

OTHER PUBLICATIONS

U.S. Appl. No. 12/286,913, Response filed Dec. 28, 2011 to Non Final Office Action mailed Sep. 28, 2011, 3 pgs,.
U.S. Appl. No. 12/226,763, Response filed Dec. 21, 2011 to Non Final Office Action mailed Aug. 22, 2011, 11 pgs.
U.S. Appl. No. 12/226,763, Final Office Action mailed Jan. 10, 2012, 16 pgs.
U.S. Appl. No. 12/229,225, Final Office Action Mailed Jan. 6, 2012, 7 pgs.
U.S. Appl. No. 12/976,344, Notice of Allowance mailed Feb. 23, 2012, 7 pgs.
U.S. Appl. No. 11/729,632, Notice of Allowance mailed Nov. 16, 2009, 7 pgs.
U.S. Appl. No. 12/286,913, Non Final Office Action mailed Mar. 1, 2012, 7 pgs.
U.S. Appl. No. 12/976,344, Notice of Allowance mailed Mar. 27, 2012, 8 pgs.
U.S. Appl. No. 12/226,763, Notice of Allowance mailed May 29, 2012, 9 pgs.
Canadian Application Serial No. 2,650,860, Office Action mailed Oct. 24, 2011, 3 pgs.
Canadian Application Serial No. 2,760,840, Office Action mailed Mar. 28, 2012, 3 pgs.
Canadian Application Serial No. 2,650,860, Response filed Apr. 23, 2012 to Office Action mailed Nov. 14, 2011, 10 pgs.
Canadian Application Serial No. 2,762,985, Office Action mailed Mar. 13, 2012, 4 pgs.
Canadian Application Serial No. 2,650,860, Office Action mailed Jun. 18, 2012, 2 pgs.
Chinese Application Serial No. 200780025394.4, Office Action mailed Oct. 13, 2011, 11 pgs.
European Application Serial No. 10778488.6, Office Action mailed Dec. 30, 2011, 2 pgs.
European Application Serial No. 11162906.9, Office Action mailed Jan. 16, 2012, 2 pgs.
European Application Serial No. 07776479.3, Office Action mailed May 30, 2012, 6 pgs.
Indian Application Serial No. 5933/CHENP/2008, Response filed Sep. 14, 2011 to Office Action mailed Oct. 14, 2010, 11 pgs.
International Application Serial No. PCT/US2010/046525, Preliminary Report on Patentability mailed Mar. 8, 2012, 6 pgs.
International Application Serial No. PCT/US2007/010415, International Search Report mailed Oct. 11, 2007, 2 pgs.
International Application Serial No. PCT/US2010/046525, Search Report mailed Apr. 29, 2011, 5 pgs.
International Application Serial No. PCT/US2010/046525, Written Opinion mailed Apr. 29, 2011, 4 pgs.
International Application Serial No. PCT/US2007/010415, Written Opinion mailed Oct. 11, 2007, 4 pgs.
ADAOA, P. et al., "Compression Characteristics of Selected Ground Agricultural Biomass", Agricultural Engineering International: The CIGR Ejournal, Manuscript 1347, vol. XI, (Jun. 2009), 19 pgs.
Alizadeh, H et al., "Pretreatment of switchgrass by ammonia fiber explosion (AFEX)", Applied Biochemistry and Biotechnology, vol. 121-124, (2005), 1133-1142.
Carolan, Joseph E., et al., "Technical and Financial Feasibility Analysis of Distributed Bioprocessing Using Regional Biomass Pre-Processing Centers", Journal of Agricultural & Food Industrial Organization, vol. 5, Article 10, (2007), 1-29.
Chahal, D. S., "Bioconversion of Hemicelluloses into Useful Products in an Intergrated Process for Food/Feed and Fuel (Ethanol) Production from Biomass", Hemicellulose Bioconversion, Biotechnol, Bioeng. Symp., (1984), 425-433.
Chang, Shu-Ting, "The World Mushroom Industry: Trends and Technological Development", International Journal of Medicinal Mushrooms, (2006), 297-314.
De Ferrer, Sulbaran B., "No. 6 Sugar Production from Rice Straw", Suppl. 1, Arch Latinoam Prod Anim 5, (1997), 112-114.
Kaliyan, N. et al., "Roll Press Briquetting and Pelleting of Corn Stover and Switchgrass", Transactions of the ASABE, vol. 52, No. 2, (2009), 543-555.
Kumar, Parveen et al., "Methods for Pretreatment of Lignocellulosic Biomass for Efficient Hydrolysis and Biofuel Production", Ind. Eng. Chem. Res., vol. 48, No. 8, (Mar. 20, 2009), 3713-3729.
Miller, Norman, "Re: Commitment Letter "Phase I Biomass Enhanced Refined Lignite Demonstration Project"", http://www.nd.gov/ndic/renew/meeting0903/r005-a-prop.pdf,(Dec. 2008), 24 pgs.
Mosier, Nathan, "Features of Promising Technologies for Pretreatment of Lignocellulosic Biomass", Bioresource Technology, vol. 96, No. 6, (Apr. 2005), 673-686.
Perry, John H., "Reactor Design", Chemical Engineers' Handbook, 4th Edition, (1969) 4-21-4-24.
Teymouri, Farzaneh et al., "Optimization of the Ammonia Fiber Explosion (AFEX) Treatment Parameters for Enzymatic Hydrolysis of Corn Stover", Bioresource Technology, vol. 96, (2005), 2014-2018.
Wilson, Jonathan, "A Cost Analysis for the Densification and Transportation of Cellulosic Biomass for Ethanol Production", Thesis for Department of Grain Science and Industry, 86 pgs., 2009.
"Topic 3 R&D on Processes for Solid, Liquid and Gaseous Fuels from Biomass", 20th EU BC&E, 26 pgs. 2012.
U.S. Appl. No. 12/226,763, Notice of Allowance Mailed Oct. 1, 2012.
U.S. Appl. No. 12/226,763, Notice of Allowance Mailed Jan. 22, 2013.
U.S. Appl. No. 12/286,913, Noitce of Allowance Mailed Oct. 3, 2012.
U.S. Appl. No. 12/763,102, Office Action Mailed Sep. 17, 2012.
U.S. Appl. No. 12/763,102, Response Filed Oct. 17, 2012 to Office Action Mailed Sep. 17, 2012.
U.S. Appl. No. 12/763,102, Office Action Mailed Dec. 24, 2012.
U.S. Appl. No. 12/791,703, Response Filed Oct. 11, 2012 to Office Action Mailed Jul. 27, 2012.
U.S. Appl. No. 13/202,011, Office Action Mailed Sep. 27, 2012.

(56) References Cited

OTHER PUBLICATIONS

U.S. Appl. No. 13/202,011, Response Filed Dec. 21, 2012 to Office Action Mailed Sep. 27, 2012.
Australian Application Serial No. 2011201768, Examination Report Mailed Jun. 21, 2012.
Australian Application Serial No. 2012249409, Examination Report Mailed Aug. 30, 2012.
Canadian Application Serial No. 2,737,704, Office Action Mailed Jun. 4, 2012.
Canadian Application Serial No. 2,737,704, Response Filed Aug. 22, 2012 to Office Action Mailed Jun. 4, 2012.
Canadian Application Serial No. 2,737,704, Office Action Mailed Nov. 5, 2012.
Canadian Application Serial No. 2,737,704, Response Filed Jan. 30, 2013 to Office Action Mailed Nov. 5, 2012.
Canadian Application Serial No. 2,737,704, Office Action Mailed Feb. 21, 2013.
Canadian Application Serial No. 2,760,840, Response Filed Jun. 27, 2012 to Office Action Mailed Mar. 28, 2012.
Canadian Application Serial No. 2,760,840, Office Action Mailed Aug. 6, 2012.
Canadian Application Serial No. 2,760,840, Response Filed Nov. 6, 2012 to Office Action Mailed Aug. 6, 2012.
Canadian Application Serial No. 2,760,840, Office Action Mailed Jan. 3, 2013.
Canadian Application Serial No. 2,650,860, Response Filed Dec. 13, 2012 to Office Action Mailed Jun. 18, 2012.
Canadian Application Serial No. 2,762,985, Response Filed Jun. 12, 2012 to Office Action Mailed Mar. 13, 2012.
Canadian Application Serial No. 2,762,985, Office Action Mailed Jul. 6, 2012.
Canadian Application Serial No. 2,762,985, Response Filed Oct. 5, 2012 to Office Action Mailed Jul. 6, 2012.
Chinese Application Serial No. 201110097994.X Office Action Mailed Jul. 30, 2012.
Chinese Application Serial No. 200780025394.4 Office Action Mailed Oct. 30, 2012.
Chinese Application Serial No. 200780025394.4 Response Filed Jan. 14, 2013 to Office Action Mailed Oct. 30, 2012.
European Application Serial No. 07776479.3, Office Action Mailed May 12, 2012.
European Application Serial No. 07776479.6, Response Filed Sep. 30, 2012 to Office Action Mailed May 30, 2012.
International Application Serial No. PCT/US2011/061617, International Search Report Mailed Jun. 8, 2012.
International Application Serial No. PCT/US2011/066868, Written Opinion Mailed Sep. 19, 2012.
Mexican Application Serial No. MX/a/2011/012357, Office Action Mailed Apr. 12, 2012.
Adapa, Phani et al., "Pelleting Characteristics of Selected Biomass With and Without", Int J Agrc & Biol Eng, Sep. 2010, vol. 3 (3), 62-79.
Bergner, Hans, "Archives of Animal Nutrition", vol. 30, 1980, 19pgs.
Cen, Peilin et al., "Production of Cellulase by Solid-State Fermentation", Advances in Biochemical Engineering/Biotechnology, vol. 65, 1999, 24pgs.
Chahal, Devinder S. et al., "Production of Cellulase in Solid-State Fermentation with *Trichoderma reesei* MCG 80 on Wheat Straw", Applied Biochemistry and Biotechnology, vol. 57/58, 1996, 10pgs.
Chinedu Nwodo, S., et al., "Xylanase Production of *Aspergillus niger* and *Penicillum chrysogenum* from Ammonia Pretreated Cellulosic Waste", Research Journal of Microbiology, vol. 3 (4), 2008, 246-253.
Chundawat, Shishir P.S. et al., "Multi-scale Visualization and Characterization of Lignocellulosic Plant Cell Wall Deconstruction During Thermochemical Pretreatment", Energy & Environmental Science, 2011, 4, 973-984.
Deshusses, Marc A. et al., "Biological Waste Air Treatment in Biofilters", Current Opinion in Biotechnology, 8, 1997, 335-339.

Kumar, Linoj et al., Does Densification Influence the Steam Pretreatment and Enzymatic Hydrolysis of Softwoods to Sugars?, Bioresource Technology, 2012, 38pgs.
Laureano-Perez, Lizbeth et al., " Understanding Factors that Limit Enzymatic Hydrolysis of Biomass" Applied Biochemistry and Biotechnology 2005, 181-124, pgs. 1081-1099.
Lu, Yanpin et al., "Cellulase Absorption and an Evaluation of Enzyme Recycle During Hydrolysis of Steam-Exploded Softwood Residues", Applied Biochemistry and Biotechnology, vols. 98-100, 2002, 14pgs.
Lynd, Lee R. et al., "Microbial Cellulose Utilization: Fundamentals and Biotechnology", Microbiology and Molecular Biology Reviews, Sep. 2002, 506-577.
Rijal, Binod et al., "Combined Effect of Pelleting and Pretreatment on Enzymatic Hydrolysis of Switchgrass", Bioresource Technology, 116, 2012, 36-41.
Sheridan, B.A. et al., "Assessment of the Influence of Media Particle Size on the Biofiltration of Odorous Exhaust Ventilation Air From a Piggery Facility", Bioresource Technology, 84, 2002, 129-143.
Singhania, Reeta Rani et al., "Advancement and Comparative Profiles in the Production Technologies Using Solid-State and Submerged Fermentation for Microbial Cellulases", Enzyme and Microbial Technology, 46, 2010, 541-549.
Theerarattananoon, Karnnalin et al., "Effect of the Pelleting Conditions on Chemical Composition and Sugar Yield of Corn Stover, Big Bluestem, Wheat Straw, and Sorghum Stalk Pellets", Bioprocess Biosyst Eng, 35, 2012, 615-623.
Tabil, Lope et al., " Biomass Feedstock Pre-Processing—Part 1: Pre-Treatment", Biofuel's Engineering Process Technology, Aug. 2011, 411-437.
Tolan, Jeffrey S., "Iogen's Demonstration Process for Producing Ethanol from Cellulosic Biomass", Biorefineries—Industrial Processes and Products. Status Quo and Future Directions, vol. 1, 2006, 16pgs.
Warzywoda, Michel et al., "Production and Characterization of Cellulolytic Enzymes from *Trichoderma reesei* Grown on Various Carbon Sources", Bioresource Technology, 39, 1992, 125-130.
Zhang, Xianglan et al., "The Effect of Different Treatment Conditions on Biomass Binder Preparation for Lignite Briquette", Fuel Processing Technology, 73, 2001, 185-196.
Sun et al., "Hydrolysis of Lignocellulosic Materials for Ethanol Production: A Review", Bioresource Technology, vol. 83, No. 1, 2002, pp. 1-11.
SunOpta, BioProcess Group, "SunOpta BioProcess Solutions" A Leader in the Processing of Value added Compounds from Plant Biomass Materials, 2007, 20 pages.
Suto et al., "Induction and Catabolite Repression Mechanisms of Cellulase in Fungi", Journal of Bioscience and Bioengineering, vol. 92, No. 4, 2001, pp. 305-311.
Taniguchi et al., "Evaluation of Pretreatment with Pleurotus Ostreatus for Enzymatic Hydrolysis of Rice Straw", Journal of Bioscience and Bioengineering, vol. 100, No. 6, Dec. 2005, pp. 637-643.
Turner et al., "Disruption of Forage Structure with an Ammonia Fiber Explosion Process", Proceedings Western Section, American Society of Animal Science, vol. 41, 1990, pp. 494-497.
Uraki et al., "Body Temperature-Responsive Gels Derived from Hydroxypropylcellulose Bearing Lignin II: Adsorption and Release Behavior", Cellulose, vol. 13, No. 3, Jun. 2006, pp. 225-234.
Urribarri et al., "Leaf Protein from Ammonia-Treated Dwarf Elephant Grass (*Pennisetum purpureum* Schum cv. Mott)", Applied Biochemistry and Biotechnology, vol. 121-124., 2005, pp. 721-730.
Van Horn et al., "Complete Rations for Growing Dairy Replacements Utilizing By-Product Feedstuffs", Journal of Dairy Science, vol. 63, 1980, pp. 1465-1474.
Vrije et al., "Pretreatment of Miscanthus for Hydrogen Production by Thermotoga Elfii", International Journal of Hydrogen Energy, vol. 27, 2002, pp. 1381-1390.
Waiss et al., "Improving Digestibility of Straws for Ruminant Feed by Aqueous Ammonia", Journal of Animal Science, vol. 35, No. 1, 1972, pp. 109-112.

(56) References Cited

OTHER PUBLICATIONS

Wang et al., "Cost Estimates and Sensitivity Analyses for the Ammonia Fiber Explosion Process", Applied Biochemistry and Biotechnology, vol. 70-72, 1998, pp. 51-66.
Wheals et al., "Fuel Ethanol after 25 Years", Trends in Biotechnology, Department of Biology and Biochemistry, University of Bath, Bath, UK, vol. 17, No. 12, Dec. 1999, pp. 482-487.
Williams et al., "An Initial Assessment of Spent Mushroom Compost as a Potential Energy Feedstock", Bioresource Technology, Vol. 79, No. 3, Sep. 2001, pp. 227-230.
Wyman et al., "Comparative Sugar Recovery Data From Laboratory Scale Application of Leading Pretreatment Technologies to Corn Stover", Bioresource Technology, vol. 96, 2005, pp. 2026-2035.
Wyman et al., "Coordinated Development of Leading Biomass Pretreatment Technologies", Bioresource Technology, vol. 96, 2005, pp. 1959-1966.
Ye et al., "Improving Accessibility and Reactivity of Celluloses of Annual Plants for the Synthesis of Methylcellulose", Cellulose, vol. 12, No. 5, Oct. 2005, pp. 507-515.
Zhang et al., "A Transition from Cellulose Swelling to Cellulose Dissolution by O-Phosphoric Acid: Evidence from Enzymatic Hydrolysis and Supramolecular Structure", Biomacromolecules, vol. 7, No. 2, Feb. 2006, pp. 644-648.
Zhang et al., "Oyster Mushroom Cultivation with Rice and Wheat Straw", Bioresource Technology, vol. 82, No. 3, May 2002, pp. 277-284.
Zhang et al., "Toward an Aggregated Understanding of Enzymatic Hydrolysis of Cellulose: Noncomplexed Cellulase Systems", Biotechnology and Bioengineering, vol. 88, No. 7, Dec. 30, 2004, pp. 797-824.
Zhong et al., "Optimization of Enzymatic Hydrolysis and Ethanol Fermentation from AFEX-Treated Rice Straw", Applied Microbiology and Biotechnology, vol. 84, 2009, pp. 667-676.
Zhou et al., "Gene Integration and Expression and Extracellular Secretion of Erwinia chrysanthemi Endoglucanase CelY (celY) and CelZ (celZ) in Ethanologenic *Klebsiella oxytoca* P2", Applied and Environmental Microbiology, vol. 67, No. 1, Jan. 2001, pp. 6-14.
Zhu et al., "Concurrent Downflow Circulating Fluidized Bed (Downer) Reactors—A State of the Art Review", The Canadian Journal of Chemical Engineering, vol. 73, Oct. 1995, pp. 662-677.
Final Office Action received for U.S. Appl. No. 12/763,102, mailed on Aug. 5, 2013, 12 pages.
Non Final Office Action Response filed for U.S. Appl. No. 12/763,102, filed on Mar. 25, 2013, 42 pages.
Non Final Office Action Response filed for U.S. Appl. No. 12/976,344, filed on Sep. 5, 2013, 16 pages.
Request for Continued Examination filed for U.S. Appl. No. 13/202,011, filed on Jul. 3, 2013, 11 pages.
Preliminary Amendment filed for U.S. Appl. No. 13/458,830, filed on Apr. 12, 2013, 26 pages.
Advisory Action received for U.S. Appl. No. 13/591,092, mailed on Jun. 6, 2013, 6 pages.
Final Office Action received for U.S. Appl. No. 13/591,092, mailed on Mar. 25, 2013, 22 pages.
Non Final Office Action Response filed for U.S. Appl. No. 13/591,092, filed on Mar. 13, 2013, 11 pages.
Preliminary Amendment filed for U.S. Appl. No. 13/886,021, filed on Jul. 25, 2013, 4 pages.
Response to the EPO Official Communication received for European patent Application No. 07776479.3, filed on Apr. 5, 2013, 13 pages.
Response to the EPO Official Communication received for European Patent Application No. 10814256.3, filed on Aug. 7, 2013, 16 pages.
Amendment filed for Indian Patent Application No. 110/DELNP/2012, filed on May 14, 2013, 55 pages.
Response to the EPO Official Communication received for European Patent Application No. 11162906.9, filed on Jul. 7, 2013, 13 pages.
Final Office Action Response filed for U.S. Appl. No. 12/763,102, filed on Oct. 7, 2013, 14 pages.
Response to the Examination Report received for Australian Patent Application No. 2010249409, filed on Aug. 27, 2013, 20 pages.
Response to the Official Communication received for Australian Patent Application No. 2010249409, filed on Aug. 28, 2013, 12 pages.
Office Action received for Chinese Patent Application No. 201110097994X, mailed on Mar. 27, 2013, 7 pages.
Official Communication received for European Patent Application No. 11162906.9, under Article 94(3) EPC, mailed on Mar. 6, 2013, 5 pages.
Response to Examination Report received for Australian Patent Application No. 2011201768, filed on Aug. 1, 2013, 46 pages.
Response to Office Action received for Canadian Patent Application No. 2760840, filed on Oct. 22, 2013, 20 pages.
Amendment after Allowance filed for Canadian Patent Application No. 2650860, filed on Jun. 13, 2013, 12 pages.
Amendment after Allowance filed for Canadian Patent Application No. 2650860, filed on May 27, 2013, 8 pages.
Notice of Allowance received for Canadian Patent Application No. 2650860, mailed on Apr. 2, 2013, 1 page.
Response filed for Canadian Patent Application No. 2737704, filed on May 21, 2013, 12 pages.
Supplemental Amendment for Canadian Patent Application No. 2737704, filed on Jul. 30, 2013, 57 pages.
Office Action received for Canadian Patent Application No. 2760840, mailed on Jul. 30, 2013, 4 pages.
Response to summons to attend oral proceedings for European Patent Application No. 07776479.3, field on Oct. 21, 2013, 16 pages.
Official Communication received for European Patent Application No. 10814256.3, under Article 94(3) EPC, mailed on Sep. 6, 2013, 4 pages.
Office Action received for Mexican Patent Application No. MX/a/2011/012357, mailed on Mar. 13, 2013, 4 pages.
International Preliminary Report on Patentability received for PCT Application No. PCT/US2011/066868, mailed on Jul. 4, 2013, 5 pages.
International Search Report received for PCT Application No. PCT/US2012/059898, mailed on Jul. 26, 2013, 4 pages.
Sokhansanj et al., "Biomass Densification—Cubing Operations and Costs for Corn Stover", Appied Engineering in Agriculture, vol. 20, No. 4, 2004, pp. 495-499.
Summons to attend oral proceedings for European Patent Application No. 07776479.3, mailed on May 7, 2013, 5 pages.
Office Action received for Chinese Patent Application No. 201210287568.7, mailed on Jul. 26, 2013, 3 pages.
Response filed for Canadian Patent Application No. 2760840, filed on May 16, 2013, 57 pages.
Jeoh et al., "Cooperative and Competitive Binding in Synergistic Mixtures of *Thermobifida fusca* Cellulases CE15A, CE16B, and CE19A", Biotechnol. Prog., vol. 18, No. 4, 2002, pp. 760-769.
Jin et al., "Two-Step SSCF to Convert AFEX-Treated Switchgrass to Ethanol using Commercial Enzymes and *Saccharomyces cerevisiae* 424A (LNH-ST)", Bioresource Technology, vol. 101, No. 21, Nov. 2010, pp. 8171-8178.
Kamm et al., "Principles of Biorefineries", Applied Microbiology and Biotechnology, vol. 64, 2004, pp. 137-145.
Karunanandaa et al., "Botanical Fractions of Rice Straw Colonized by White-Rot Fungi: Changes in Chemical Composition and Structure", Animal Feed Science Technology, vol. 55, 1995, pp. 179-199.
Keller et al., "Microbial Pretreatment of Biomass potential for Reducing Severity of Thermochemical Biomass Pretreatment", Applied Biochemistry and Biotechnology, vol. 105-108, 2003, pp. 27-41.
Kim et al., "Enhancement of the Enzymatic Digestibility of Waste Newspaper Using Tween", Applied Biochemistry and Biotechnology, vol. 129-132, 2006, pp. 486-495.
Kim et al., "Lime Pretreatment and Enzymatic Hydrolysis of Corn Stover", Bioresource Technology, vol. 96, 2005, pp. 1994-2006.
Kim et al., "Pretreatment and Fractionation of Corn Stover by Ammonia Recycle Percolation Process", Bioresource Technology, vol. 96, No. 18, 2005, pp. 2007-2013.
Knauf et al., "Lignocellulosic Biomass Processing: A Perspective", International Sugar Journal, vol. 106, No. 1263, 2004, pp. 147-150.
Kudra et al., "Advanced Drying Technologies", Superheated Steam Drying, Marcel Dekker, Inc., New York, Basel, NY, 2002, pp. 81-111.

(56) References Cited

OTHER PUBLICATIONS

Ladisch et al., "Building a Bridge to the Ethanol Industry-Follow-Up Project", Subcontractor Report, National Renewable Energy Laboratory, Apr. 2003, 36 pages.
Lau et al., "Cellulosic Ethanol Production from AFEX-treated Corn Stover Using *Saccharomyces cerevisiae* 424A (LNH-ST)", PNAS, vol. 106, No. 5, Feb. 3, 2009, pp. 1368-1373.
Lau et al., "Comparing the Fermentation Performance of *Escherichia coli* KO11, *Saccharomyces cerevisiae* 424A (LNH-ST) and *Zymomonas mobilis* AX101 for Cellulosic Ethanol Production", Biotechnology for Biofuels, vol. 3, No. 11, 2010, pp. 1-10.
Lau et al., "Ethanol Fermentation of *E. coli* KO11 in Hydrolysate from AFEX-treated Corn Stover", Biomass Conversion Research Laboratory, Department of Chemical Engineering and Materials Science, Michigan State University, 1 page.
Lau et al., "The Impacts of Pretreatment on the Fermentability of Pretreated Lignocellulosic Biomass: A Comparative Evaluation between Ammonia Fiber Expansion and Dilute Acid Pretreatment", Biotechnology for Biofuels, vol. 2, No. 30, Dec. 2009, 10 pages.
Lin et al., "Ethanol Fermentation From Biomass Resources: Current State and Prospects", Applied Microbiology and Biotechnology, vol. 69, No. 6., Feb. 2006, pp. 627-642.
Liu et al., "Partial Flow of Compressed-Hot Water through Corn Stover to Enhance Hemicellulose Sugar Recovery and Enzymatic Digestibility of Cellulose", Bioresource Technology, vol. 96, No. 18, 2005, pp. 1978-1985.
Lloyd et al., "Combined Sugar Yields for Dilute Sulfuric Acid Pretreatment of Corn Stover Followed by Enzymatic Hydrolysis of the Remaining Solids", Bioresource Technology, vol. 96, No. 18, Dec. 2005, pp. 1967-1977.
Lovrien et al., "Assays for Total Protein", Basic Protocol 1, Unit 34, Current Protocols in Protein Science, John Wiley & Sons, Inc., 1995, 24 pages.
Madakadze et al., "Cutting Frequency and Nitrogen Fertilization Effects on Yield and Nitrogen Concentration of Switchgrass in a Short Season Area", Crop Science, vol. 39, 1999, pp. 552-557.
Mani et al., "Economics of Producing Fuel Pellets from Biomass", Applied Engineering in Agriculture, vol. 22, No. 3, American Society of Agricultural and Biological Engineers, 2006, pp. 421-426.
Mantanis et al., "Swelling of Compressed Cellulose Fiber Webs in Organic Liquids", Cellulose, vol. 2, 1995, pp. 1-22.
Marshall et al., "Complete Rations for Dairy Cattle. II. Sugarcane Bagasse Pellets as Roughage in Blended Rations for Lactating Cows", Journal of Dairy Science vol. 58, No. 6, Jun. 1975, pp. 896-900.
Martinez et al., "Biodegradation of Lignocellulosics: Microbial, Chemical, and Enzymatic Aspects of the Fungal Attack of Lignin", International Microbiology, vol. 8, 2005, pp. 195-204.
Mosier et al., "Optimization of pH Controlled Liquid Hot Water Pretreatment of Corn Stover", Bioresource Technology, vol. 96, 2005, pp. 1986-1993.
Obodai et al., "Comparative Study on the Growth and Yield of Pleurotus Ostreatus Mushroom on Different Lignocellulosic By-Products", Journal of Industrial Microbiology and Biotechnology, vol. 30, No. 3, 2003, pp. 146-149.
O'Connor, James J., "Ammonia Explosion Pulping : A New Fiber Separation Process", Tappi, vol. 55, No. 3, Mar. 1972, pp. 353-358.
Ohara, H., "Biorefinery", Applied Microbiology and Biotechnology, vol. 62, No. 5-6, Oct. 2003, pp. 474-477.
Ordonez et al., "Obtaining a Protein Concentrate From Integral Defatted Sunflower Flour", Bioresource Technology, vol. 78, No. 2, 2001, pp. 187-190.
Ozturk et al., "Splitting Tendency of Cellulosic Fibers. Part 2: Effects of Fiber Swelling in Alkali Solutions", Cellulose, vol. 13, No. 4, Aug. 2006, pp. 403-409.
Pandey et al., "Economic Utilization of Crop Residues for Value Addition: A Futuristic Approach", Journal of Scientific & Industrial Research, vol. 59, Jan. 2000, pp. 12-22.

Park et al., "Investigation and Optimization of the Factors Influencing Sorghum Protein Extraction", Journal of Agricultural and Food Chemistry, vol. 51, No. 24, Oct. 2003, pp. 7050-7054.
Paul et al., "Liquid-Vapor Interfacial Properties of Water-Ammonia Mixtures: Dependence on Ammonia Concentration", J. Chem. Phys., vol. 123, No. 17, 174712, 2005, pp. 174712-1-174712-9.
Poppe, J., "Use of Agricultural Waste Materials in the Cultivation of Mushrooms" Science and Cultivation of Edible Fungi, vol. 1&2, 2000, pp. 3-23.
Ragauskas et al., "The Path Forward for Biofuels and Biomaterials", Science, vol. 311, Jan. 27, 2006, pp. 484-489.
Rajagopalan et al., "Enhancing Profitability of Dry Mill Ethanol Plants", Applied Biochemistry and Biotechnology, vol. 120, No. 1, 2005, pp. 37-50.
Rausch et al., "The Future of Coproducts from Corn Processing", Applied Biochemistry and Biotechnology, vol. 128, 2006, pp. 47-86.
Renewable Fuels Association, "From Niche to Nation: Ethanol Industry Outlook", 2006 Renewable Fuels Association, Washinton DC, 2006, 24 pages.
Rollin et al., "Increasing Cellulose Accesibility is More Important than Removing Lignin: A Comparison of Cellulose Solvent-Based Lignocellulose Fractionation and Soaking in Aqueous Ammonia", Biotechnology and Bioengineering, vol. 108, No. 1, Jan. 2011, pp. 22-30.
Roman-Ponce et al., "Complete Rations for Dairy Cattle. V. Interaction of Sugarcane Bagasse Quantity and Form with Soybean Meal, Urea, and Starea", Journal of Dairy Science, vol. 58, No. 9, Sep. 1975, pp. 1320-1327.
Rosa et al., "Integrated Production of Ethanol Fuel and Protein from Coastal Bermudagrass", Applied Biochemistry and Biotechnology, vol. 45-46, No. 1, 1994, pp. 483-497.
Saha, Badal C., "Hemicellulose Bioconversion", Journal of Industrial Microbiology and Biotechnology, vol. 30, No. 5, May 2003, pp. 279-291.
Sanchez et al., "Biodegradation of Viticulture Wastes by Pleurotus: A Source of Microbial and Human Food and Its Potential Use in Animal Feeding", J. Agric. Food Chem., vol. 50, No. 9, Apr. 24, 2002, pp. 2537-2542.
Sanderson et al., "Switchgrass as a Sustainable Bioenergy Crop", Bioresource Technology, vol. 56, Apr. 1996, pp. 83-93.
Sarikaya et al., "Solid-State Fermentation of Lignocellulosic Plant Residues from *Brassica napus* by *Pleurotus ostreatus*", Applied Biochemistry and Biotechnology, vol. 82, No. 1, Oct. 1999, pp. 1-15.
Singh et al., "Composting of a Crop Residue through Treatment with Microorganisms and Subsequent Vermicomposting", Bioresource Technology, vol. 85, No. 2, Nov. 2002, pp. 107-111.
Sluiter et al., "Determination of Structural Carbohydrates and Lignin in Biomass", National Renewable Energy Laboratory, Technical Report, N REL/TP-51 0-42618, Apr. 25, 2008, 17 pages.
Steele et al., "Enzyme Recovery and Recycling Following Hydrolysis of Ammonia Fiber Explosion—Treated Corn Stover", Applied Biochemistry and Biotechnology, vol. 121-124, No. 1-3, 2005, pp. 901-910.
Sukumaran et al., "Cellulase Production using Biomass Feed Stock and its Application in Lignocellulose Saccharification for Bio-Ethanol Production", Renewable Energy, vol. 34, 2009, pp. 421-424.
Sulbaran-De-Ferrer et al., "Enzymatic Hydrolysis of Ammonia-Treated Rice Straw", Applied Biochemistry and Biotechnology, vol. 105-108, 2003, pp. 155-164.
Extended European Search Report received for European Patent Application No. 07776479.3 mailed on May 26, 2010, 6 pages.
Non Final Office Action received for U.S. Appl. No. 11/901,336, mailed on Apr. 27, 2010, 10 pages.
Notice of Allowance received for U.S. Appl. No. 11/901,336, mailed on Aug. 24, 2010, 5 pages.
Non Final Office Action received for U.S. Appl. No. 12/214,687, mailed on Jun. 2, 2011, 6 pages.
Non Final Office Action received for U.S. Appl. No. 12/286,913, mailed on Sep. 28, 2011, 7 pages.
Non-Final Office Action received for U.S. Appl. No. 13/591,092, mailed on Dec. 13, 2012, 13 pages.
Office Action received for Canadian Patent Application No. 2,650,860, mailed on May 12, 2011, 2 pages.

(56) References Cited

OTHER PUBLICATIONS

Office Action received for Australian Patent Application No. 2007248736, mailed on Dec. 1, 2009, 2 pages.
Office Action received for Indian Patent Application No. 5933/CHENP/2008, mailed on Oct. 29, 2010, 2 pages.
International Preliminary Report on Patentability received for PCT Patent Application No. PCT/US07/10415, completed on Aug. 1, 2008, 6 pages.
International Preliminary Report on Patentability received for PCT Patent Application No. PCT/US2007/010410, mailed on Dec. 12, 2008, 5 pages.
International Search Report received for PCT Patent Application No. PCT/US2007/010410, mailed on Jun. 10, 2008, 1 page.
Written Opinion received for PCT Patent Application No. PCT/US2007/010410, mailed on Jun. 10, 2008, 4 pages.
International Search Report received for PCT Patent Application No. PCT/US2008/011488, mailed on Jan. 8, 2009, 1 page.
Written Opinion received for PCT Patent Application No. PCT/US2008/011488, mailed on Jan. 8, 2009, 5 pages.
Allan et al., "Replacement of Fish Meal in Diets for Australian Silver Perch, Bidyanus Bidyanus: I. Digestibility of Alternative Ingredients", Aquaculture, vol. 186, No. 3-4, Jun. 2000, pp. 293-310.
Balan et al., "Mushroom Spent Straw: A Potential Substrate for an Ethanol-Based Biorefinery", Journal of Industrial Microbiology and Biotechnology, vol. 35, No. 5, 2008, pp. 293-301.
Baldrian et al., "Variability of Laccase Activity in the White-Rot Basidiomycete *Pleurotus ostreatus*", Folia Microbiologica, vol. 47, No. 4, 2002, pp. 385-390.
Bals et al., "Enzymatic Hydrolysis of Distiller's Dry Grain and Solubles (DDGS) Using Ammonia Fiber Expansion Pretreatment", Energy & Fuels, vol. 20, No. 6, 2006, pp. 2732-2736.
Beale et al., "Leaf Photosynthesis in the C4-Grass Miscanthus X giganteus, Growing in the Cool Temperate Climate of Southern England", Journal of Experimental Botany, vol. 47, No. 295, Feb. 1996, pp. 267-273.
Belyea et al., "Element Concentrations of Dry-Grind Corn-Processing Streams", Applied Biochemistry and Biotechnology, vol. 134, No. 2, 2006, pp. 113-128.
Betschart et al., "Extractability and Solubility of Leaf Protein", J. Agr. Food Chem., vol. 21, No. 1, 1973, pp. 60-65.
Boluk, Yaman, "Acid-Base Interactions and Swelling of Cellulose Fibers in Organic Liquids", Cellulose, vol. 12, No. 6, Dec. 2005, pp. 577-593.
Bothast et al., "Biotechnological Processes for Conversion of Corn into Ethanol: Enzymology and Mechanisms Involved" Appl. Microbiol. Biotechnol., vol. 67, No. 1, 2005, pp. 19-25.
Christian et al., "Degradation of Xenobiotic Compounds by Lignin-Degrading White-Rot Fungi", Indian Journal of Experimental Biology, vol. 43, Apr. 2005, pp. 301-312.
Chundawat et al., "Effect of Particle Size Based Separation of Milled Corn Stover on AFEX Pretreatment and Enzymatic Digestibility", Biotechnology and Bioengineering, vol. 96, No. 2, Feb. 1, 2007, pp. 219-231.
Chundawat, Shishir Pratap Singh, "Ultrastructural and Physicochemical Modifications within Ammonia Treated Lignocellulosic Cell Walls and their Influence on Enzymatic Digestibility", Dissertation for Michigan State University, 2010, 469 pages.
Clifton-Brown et al., "Performance of 15 Miscanthus Genotypes at Five Sites in Europe", Agronomy Journal, vol. 93, No. 5, Sep.-Oct. 2001, pp. 1013-1019.
Cohen et al., "Biotechnological Applications and Potential of Wood-Degrading Mushrooms of the Genus Pleurotus", Appl. Microbial. Biotechnol., vol. 58, 2002, pp. 582-591.
Dale et al., "Fermentation of Lignocellulosic Materials Treated by Ammonia Freeze-Explosion", Developments in Industrial Microbiology, Chapter 13, vol. 26, 1985 pp. 223-233.

Eggeman et al., "Process and Economic Analysis of Pretreatment Technologies", Bioresource Technology, vol. 96, 2005, pp. 2019-2025.
El-Adawy et al., "Nutritional Potential and Functional Properties of Sweet and Bitter Lupin Seed Protein Isolates", Food Chemistry, vol. 74, No. 4, 2001, pp. 455-462.
"Energy Policy Act of 2005", Public Law, 109-58, 109th Congress, Aug. 8, 2005, pp. 1067-1076.
Felix et al., "In Vitro and In Vivo Digestibility of Soya-Bean Straw Treated with Various Alkalis", Animal Production, vol. 51, No. 1, 1990, pp. 47-61.
Fernandez et al., "Protein Extraction from Atriplex Lampa Leaves: Potential Use as Forage for Animals used for Human Diets", Plant Foods for Human Nutrition, vol. 54, No. 3, 1999, pp. 251-259.
Ferrer et al., "Increasing Nutrient Availability of Feather Meal for Ruminants and Non-Ruminants Using an Ammonia Pressurisation/Depressurisation Process", Journal of the Science of Food and Agriculture, vol. 79, 1999, pp. 828-832.
Ferrer et al., "Optimizing Ammonia Pressurization/Depressurization Processing Conditions to Enhance Enzymatic Susceptibility of Dwarf Elephant Grass", Applied Biochemistry and Biotechnology, vol. 84-86, No. 1-9, 2000, pp. 163-179.
Fiorentini et al., "Pilot Plant Production of an Edible Alfalfa Protein Concentrate", Journal of Food Science, vol. 46, No. 5, 1981, pp. 1514-1517.
Foster et al., Enzymatic Hydrolysis of Ammonia-Treated Sugar Beet Pulp Applied Biochemistry and Biotechnology, vol. 91-93, 2001, pp. 269-282.
Fulks et al., "A Review of Solid Materials as Alternative Ammonia Sources for Lean NOx Reduction with SCR", Technical Paper No: 2009-01-0907, SAE International, 2009, 13 pages.
Gollapalli et al., "Predicting Digestibility of Ammonia Fiber Explosion (AFEX)-Treated Rice Straw", Applied Biochemistry and Biotechnology, vol. 98-100, 2002, pp. 23-35.
Gray et al., "Bioethanol", Current Opinion in Chemical Biology, vol. 10, 2006, pp. 141-146.
Greene et al., "Growing Energy: How Biofuels Can Help End America's Oil Dependence", Natural Resources Defense Council, Dec. 2004, 86 pages.
Hahn-Hagerdal et al., "Bio-Ethanol—The Fuel of Tomorrow from the Residues of Today", Trends in Biotechnology, vol. 24, No. 12, Dec. 2006, pp. 549-556.
Hanchar et al., "Separation of Glucose and Pentose Sugars by Selective Enzyme Hydrolysis of AFEX-Treated Corn Fiber", Applied Biochemistry and Biotechnology, vol. 136-140, No. 1-12, 2007, pp. 313-326.
Heaton et al., "A Quantitative Review Comparing the Yields of Two Candidate C4 Perennial Biomass Crops in Relation to Nitrogen, Temperature and Water", Biomass and Bioenergy, vol. 27, No. 1, Jul. 2004, pp. 21-30.
Heaton et al., "Miscanthus for Renewable Energy Generation: European Union Experience and Projections for Illinois", Mitigation and Adaptation Strategies for Global Change, vol. 9, No. 4, Oct. 2004, pp. 433-451.
Holtzapple et al., "The Ammonia Freeze Explosion (AFEX) Process a Practical Lignocellulose Pretreatment", Applied Biochemistry and Biotechnology, vol. 28-29, No. 1, 1991, pp. 59-74.
Houghton et al., "Fungal Upgrading of Wheat Straw for Straw-Thermoplastics Production", Applied Biochemistry and Biotechnology, vol. 113-116, 2004, pp. 71-93.
Israilides et al., "Bio-technologies of Recycling Agroindustrial Wastes for the Production of Commercially Important Fungal Polysaccharides and Mushrooms", Biotechnology and Genetic Engineering Reviews, vol. 20, Dec. 2003, pp. 247-259.

\* cited by examiner

PROCESS FOR THE TREATMENT OF LIGNOCELLULOSIC BIOMASS

CROSS-REFERENCE TO RELATED APPLICATIONS

This application is a continuation of U.S. patent application Ser. No. 12/226,763 (Issued as U.S. Pat. No. 8,394,611) filed on Oct. 27, 2008, which application is a U.S. National Stage Application of International Application No. PCT/US2007/010454 filed on Apr. 30, 2007, which application claims benefit to U.S. Provisional Application Ser. No. 60/796,375, filed May 1, 2006, each of which is incorporated herein by reference in its entirety.

STATEMENT OF GOVERNMENT RIGHTS

This invention was made with government support under XCO-3-33033-01 awarded by the United States Department of Energy and under 00-52104-9663 awarded by the United States Department of Agriculture. The government has certain rights in the invention.

FIELD

The present invention relates to a process for the treatment of a lignocellulosic biomass with concentrated ammonium hydroxide and preferably with ammonia gas to increase the availability of structural carbohydrates (polysaccharides). Preferably, steam under pressure is used to strip ammonia from the biomass for recycling. In particular, the present invention relates to a process which enables the efficient conversion of the polysaccharides to monosaccharides preferably by enzymatic hydrolysis.

BACKGROUND

A wide variety of methods (e.g. concentrated or dilute acids or bases, high temperatures, radiation of various forms) have been used to pretreat lignocellulosic biomass to extract structural carbohydrates to be used to obtain monosaccharides for many different uses. The goal of these pretreatments is to increase the rate and/or yield at which the monosaccharides are subsequently obtained from the structural carbohydrates by chemical or biochemical means such as acid catalysis, enzymatic catalysis, fermentation or animal digestion. In general, these pretreatments have fallen short of desired economic and technical performance for several reasons: 1) many pretreatments degrade some of the sugars, e.g. to acids or aldehydes, thus reducing yields and inhibiting subsequent biological conversion of the remaining sugars; 2) when chemicals are used in the pretreatment, it is frequently difficult to recover these chemicals at reasonable cost; 3) residual chemicals can negatively affect downstream conversion operations; and 4) the effectiveness of many pretreatments is limited so that the ultimate conversions of structural carbohydrates obtained, independent of lost yield by sugar degradation reactions, is inadequate for competitive process economics. Thus there are many prior art methods, and they have numerous drawbacks including those outlined above.

Sufficiently inexpensive monosaccharides from renewable plant biomass can become the basis of chemical and fuels industries, replacing or substituting for petroleum and other fossil feedstocks. Effective, economical pretreatments are required to make these monosaccharides available at high yield and acceptable cost.

The prior art in the pretreatment of plant biomass with anhydrous liquid ammonia or ammonium hydroxide solutions is extensive. Illustrative are the following patents and literature references:

U.S. Pat. No. 4,600,590 to Dale
U.S. Pat. No. 4,644,060 to Chou
U.S. Pat. No. 5,037,663 to Dale
U.S. Pat. No. 5,171,592 to Holtzapple et al.
U.S. Pat. No. 5,865,898 to Holtzapple et al.
U.S. Pat. No. 5,939,544 to Karsents et al.
U.S. Pat. No. 5,473,061 to Bredereck et al.
U.S. Pat. No. 6,416,621 to Karstens
U.S. Pat. No. 6,106,888 to Dale et al.
U.S. Pat. No. 6,176,176 to Dale et al.
Felix, A., et al., Anim. Prod, 51 47-61 (1990)
Waiss, A. C., Jr., et al., Journal of Animal Science 35 No. 1, 1.09-112 (1972). All of these patents and publications are incorporated herein in their entireties.

In particular, ammonia fiber explosion (AFEX™) (hereinafter "AFEX", now more commonly referred to as "ammonia fiber expansion") represents a unique and effective pretreatment for biologically converting lignocellulosic biomass to ethanol (Dale, B. E., 1986. U.S. Pat. No. 5,037,663; Dale, B. E., 1991. U.S. Pat. No. 4,600,590; Alizadeh, H., F. Teymouri, T. I. Gilbert, B. E. Dale, 2005. Pretreatment of Switchgrass by Ammonia Fiber Explosion. Applied Biochemistry and Biotechnology, 121-124:1133-1141; Dale, B. E., 1991. U.S. Pat. No. 4,600,590; Dale, B. E., 1986. U.S. Pat. No. 5,037,663). In AFEX pretreatment, lignocellulosic biomass is exposed to concentrated ammonia at elevated pressures sufficient to maintain ammonia in liquid phase and moderate temperatures (e.g. around 100° C.). Residence times in the AFEX reactor are generally less than 30 minutes. To terminate the AFEX reaction, the pretreated biomass is depressurized (flashed). The AFEX process is not limited to anhydrous ammonia with AFEX. Some water is added to the biomass, so that any anhydrous ammonia is immediately converted into a concentrated ammonia water mixture on beginning the AFEX treatment.

Recovery of ammonia used in AFEX pretreatment is a key objective when integrating AFEX into a broader biomass conversion process design. The existing ammonia recovery design (Eggeman, T. 2001). Ammonia Fiber Explosion Pretreatment for Bioethanol Production, National Renewable Energy Laboratory (NREL) Subcontract No. LCO-1-31055-01), which is depicted in FIG. 1, calls for compressing ammonia, which is vaporized as a result of the flash operation, and separating liquid ammonia that remains in contact with the pretreated solids via evaporation in a dryer. The resulting vapor, which also contains water, is then delivered to a distillation column to purify the ammonia. The ammonia from the column is pumped up to pressure and, together with the compressed flash ammonia, is recycled to the AFEX reactor. FIG. 1 shows the existing ammonia recovery approach.

FIG. 1 shows the prior art system 10 including a closed AFEX reactor vessel 12 into which biomass, water and ammonia are introduced under pressure. Valve $V_1$ is used to release pressure from the vessel 12. The treated biomass is transferred to a heated dryer 14. The dried biomass is transferred out of the dryer 14 for subsequent treatment. Ammonia from the dryer 14 is condensed by condenser 22 and sent to slurry column 16. Water is removed and condensed by condenser 18. Ammonia is condensed in condenser 20 and recycled to the vessel 12. Ammonia gas is pressurized in a compressor 24, condensed and recycled into vessel 12.

The problem is that the processes either produce low yields of the monosaccharides and/or require large amounts of liquid ammonia or ammonium hydroxide solutions.

OBJECTS

It is therefore an object of the present invention to provide a process which effectively combines the use of concentrated ammonium hydroxide to extract the structural carbohydrates with an effective recycling of the ammonia. Further, it is an object of the present invention to provide an economical process which enables the production of monosaccharides in high yield from the structural carbohydrates. These and other objects will become increasingly apparent by reference to the following description and the drawings.

SUMMARY

The present invention relate to a process for the treatment of structural carbohydrates in lignocellulosic biomass which comprises: (a) reacting the biomass with a heated aqueous ammonium hydroxide solution having a concentration greater than about 30% by weight ammonia in a closed vessel at 50° C. or above at an elevated pressure from atmospheric pressure while simultaneously manipulating the temperature, a mass ratio of ammonia to a dry biomass and a mass ratio of water to the dry biomass to increase the digestibility and/or accessibility of the structural carbohydrates; (b) rapidly releasing the pressure in the vessel; (c) recovering at least some of the ammonia and ammonium hydroxide from the biomass and the solution; and (d) optionally further processing the treated biomass via enzymes, microbial conversion or animal digestive processes. Preferably the structural carbohydrates are recovered as a mixture of glucose, xylose, arabinose and other sugars in step (d). Preferably the structural carbohydrates made available by the further treatment which is the microbial conversion which produces organic acids, alcohols, and other byproducts. Preferably the carbohydrates made available by the process are utilized by the animal digestive processes in either ruminant or non-ruminant animal diets. Preferably the temperature of the mixture of ammonia, biomass and water in the closed vessel is at a temperature between about 50° C. and 120° C. Preferably the pressure in the closed vessel is between about 4 and 50 atm. Preferably ammonia gas is added to the vessel to fill any void space in the vessel. The ammonia treatment does not directly solubilize very much of the biomass. About 20% or so of the hemicellulose (xylan polymer primarily) can be solubilized, but essentially none of the glucan structural polysaccharides (cellulose) are solubilized. What happens is that they are "activated" or rendered much more susceptible to hydrolysis. The term "structural carbohydrates" means cellulose and hemicellulose.

The present invention also relates to a process for the treatment of a lignocellulosic containing plant biomass comprising structural carbohydrates with water naturally present in the biomass to produce more digestible or accessible structural carbohydrates which comprises: (a) reacting the biomass with a heated aqueous ammonium hydroxide solution in an amount greater than about 30% by weight ammonia in the aqueous ammonium hydroxide solution in a closed vessel at an elevated pressure and at an elevated temperature without degrading the lignocellulose to remove the structural carbohydrates from the biomass into the solution, wherein an amount of water provided with the biomass is greater than 1% by weight and less than 50% by weight of the biomass; (b) releasing the pressure in the biomass in the vessel; (c) removing a slurry of the biomass with the structural carbohydrates from the vessel; and (d) stripping the ammonium hydroxide solution and ammonia from the slurry to provide the structural carbohydrates in the slurry, wherein greater than 85% of the available glucose in the structural carbohydrates can be recovered as a result of enzymatic hydrolysis of the structural carbohydrates. Preferably the ammonia is recycled. Preferably the sugars comprise a mixture of xylose and glucose. Preferably a temperature of the mixture of ammonia, biomass and water in the closed vessel is between about 50 and 120° C. Preferably ammonia gas is added to fill any void space in the vessel. Preferably the pressure is released rapidly. Preferably the pressure is between about 6.9 and 20.7 atm.

The present invention further relates to a process for recovery of ammonia from an ammonia fiber explosion (AFEX) treatment of a lignocellulosic biomass which comprises: (a) treating the biomass with an aqueous solution of ammonium hydroxide in a closed reaction vessel under pressure to form a slurry; (b) releasing the pressure in the vessel of the reaction vessel and pumping the slurry to a stripping column; (c) stripping ammonia from an upper portion of the stripping column, using steam under pressure with removal of a stripped slurry from a bottom portion of the column; (d) introducing the stripped ammonia from the upper portion of the column into a mixer and adding water under pressure to the mixer to form a diluted aqueous ammonia solution; (e) cooling the diluted aqueous ammonia solution from the mixer; and (f) introducing the cooled aqueous ammonia solution into the reaction vessel along with the additional biomass under pressure. Preferably, the reaction is continuous. The, present invention also relates to a system for performing the process as described herein.

The substance and advantages of the present invention will become increasingly apparent by reference to the following drawings and the description.

DESCRIPTION OF THE PREFERRED EMBODIMENTS

Cellulosic biomass contains large amounts of structural carbohydrates or polysaccharides (cellulose, hemicellulose, and the like) that can provide much less expensive single sugars for fermentation or non-biological transformation to a variety of products or as improved animal feeds. However, these polysaccharides are difficult to access. The present invention provides a pretreatment process using concentrated ammonium hydroxide under pressure to improve the accessibility/digestibility of the polysaccharides from a cellulosic biomass. The present invention preferably uses combinations of anhydrous ammonia and concentrated ammonium hydroxide solutions to obtain results that are not obtained by either dilute ammonium hydroxide or anhydrous ammonia acting alone.

In the present invention the lignocellulosic material is treated with concentrated ammonium hydroxide in an amount greater than 30% by weight in an ammonium hydroxide solution. The process can be performed in a continuous reactor or a batch reactor as in the Examples.

The biomass contains water which is naturally present. Typically this natural water represents about 1% to 20% by weight of the biomass. In general this natural water tends to be bound in the biomass and thus the water which is primarily relied upon is that added with the ammonium hydroxide solution. Water can also be added to the biomass and, if so, then this mixes with the ammonium hydroxide to provide the ammonium hydroxide solution. Up to 50% of the biomass can be added water.

The term "lignocellulosic biomass" means a naturally derived lignin and cellulose based material. Such materials are, for instance, alfalfa, wheat straw, corn stover, wood fibers, and the like. Preferably the materials are comminuted into particles in a longest dimension.

The term "structural carbohydrates" means the polysaccharide materials containing monosaccharide moieties available by hydrolysis.

The mass ratio of a lignocellulose biomass to ammonia is preferably 1 to 1.

The reaction temperature is preferably 90° C.; however the temperature can be between 50° C. and 120° C.

The pressure is preferably between 100 psia and 300 psi (6.9 to 20.7 atm); however, pressures between 4 and 50 atm can be used.

Hot ammonium hydroxide/water solutions or hot ammonia/water vapors can be added to ground lignocellulosic biomass in a contained vessel to obtain final mixture temperatures of 50° C. or above, preferably 90° C. A preferred ammonia to dry biomass mass weight ratio was about 0.2 to 1.0. A preferred water to dry biomass mass ratio was about 0.4 to 1.0.

Figure 1:
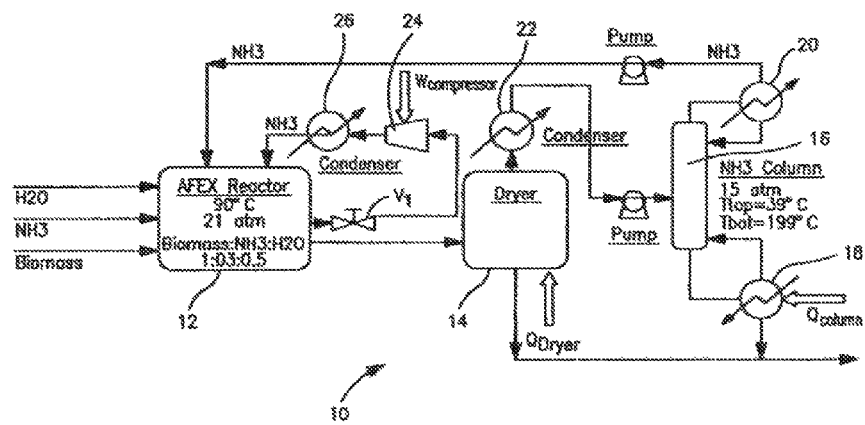
FIG. 1 is a process flow diagram for a prior art AFEX pretreatment with ammonia recovery and recycling.
Figure 2:
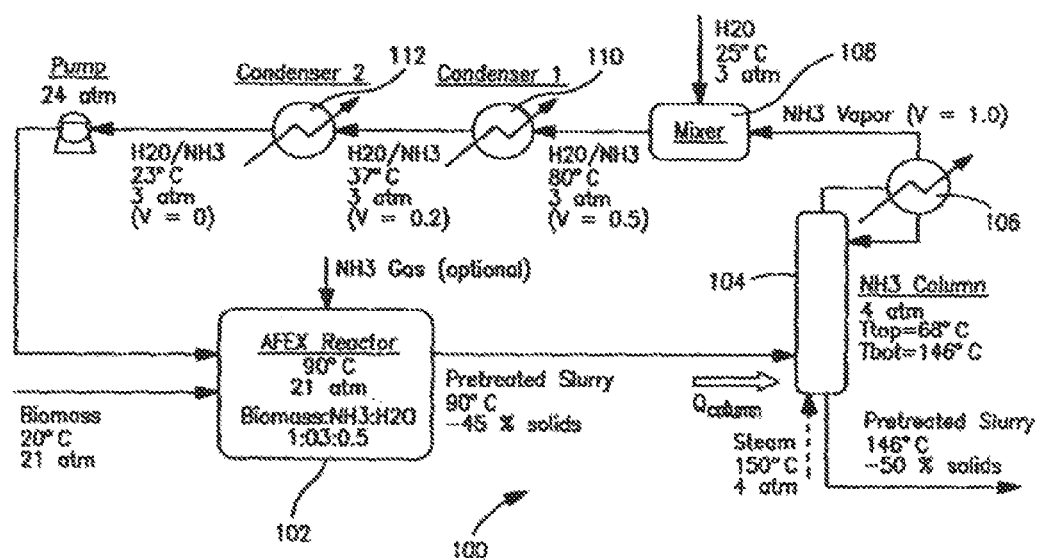
FIG. 2 is a process flow diagram for the present invention for AFEX pretreatment with an efficient ammonia recovery.

FIG. 2 shows the improved system 100 with an AFEX reactor vessel. The slurry is sent directly to the stripping column 104 and condenser in condenser 106 and is sent to mixer 108 for addition of water. High pressure steam is used in the stripping column 104 to remove the ammonia from the slurry. The hot aqueous slurry is removed from the bottom of the stripping column. Condensers 110 and 112 are used to cool the water and ammonia mixture which is recycled into the vessel 102. By comparing FIGS. 1 and 2, it can be seen that the process is more efficient.

EXAMPLES 1 TO 20

A 300 ml pressure vessel 102 was first filled with a given mass of corn stover wetted to the desired moisture level as indicated in Table 1 and the vessel 102 was sealed. Thereafter, a concentrated ammonium hydroxide mixture was prepared by mixing the right proportions of anhydrous ammonia and water in another pressure vessel. This mixture was added to the corn stover in the 300 ml reactor vessel 102 to achieve the desired final level of ammonia and water. In this case the target was 1 kg of ammonia per kg of dry biomass and 0.6 kg of water per kg of dry biomass. The mixture of ammonia, water and biomass was then heated to 90° C., held at that temperature for 5 minutes and the pressure rapidly released.

The resulting solid was hydrolyzed to mixtures of monosaccharides containing, for example, glucose, xylose and arabinose.

The results of the present invention are shown in Table 1 in Examples 2 to 15.

TABLE 1

Glucose and Xylose yields of ammonia treated corn stover after 168 hr (7 days) for hydrolysis with a cellulose enzyme. Different ammonia concentrations were used. All runs are at 1 kg NH3: 1 Kg dry stover (BM), 90° C. reactor temperature, 0.6 kg water/kg dry stover (except for the last 4 experiments 17 to 20) and 5 min residence time. 15 FPU cellulase enzyme/gram glucan in BM.

| Expt. # | Kg $NH_3$/kg water in ammonium hydroxide | Ammonia distribution | Water distribution | % Glucose yield | % Xylose yield | Repeats |
|---|---|---|---|---|---|---|
| 1(a) | 1 kg $NH_3$ | All $NH_3$ | All in BM | 92.96 | 74.25 | 2 |
| 2 | 0.5 | ¾ $NH_3$ and ¼ $NH_4OH$ | ½ in $NH_4OH$ ½ in BM | 92.20 | 78.85 | 2 |
| 3 | 0.5 | 3.4 $NH_3$ and ¼ $NH_4OH$ | All in $NH_4OH$ | 79.88 | 64.90 | 2 |
| 4 | 0.41 | ⅔ $NH_3$ and ⅓ $NH_4OH$ | All in $NH_4OH$ | 86.60 | 70.54 | 1 |
| 5 | 0.58 | ⅔ $NH_3$ and ⅓ $NH_4OH$ | ½ in $NH_4OH$ ½ in BM | 78.23 | 65.83 | 1 |
| 6 | 0.5 | ½ $NH_3$ and ½ $NH_4OH$ | All in $NH_4OH$ | 57.65 | 47.85 | 1 |
| 7 | 0.8 | ½ $NH_3$ and ½ $NH_4OH$ | ¾ in $NH_4OH$ ¼ in BM | 85.50 | 70.37 | 1 |
| 8 | 0.66 | ½ $NH_3$ and ½ $NH_4OH$ | ½ in $NH_4OH$ ½ in BM | 97.78 | 81.98 | 2 |
| 9 | 0.79 | ½ $NH_3$ and ½ $NH_4OH$ | ¾ in BM ¼ in $NH_4OH$ | 98.54 | 78.70 | 2 |
| 10 | 0.38 | ⅓ $NH_3$ and ⅔ $NH_4OH$ | All in $NH_4OH$ | 74.52 | 56.47 | 1 |
| 11 | 0.73 | ⅓ $NH_3$ and ⅔ $NH_4OH$ | ½ in $NH_4OH$ ½ in BM | 81.51 | 69.66 | 1 |
| 12 | 0.66 | All $NH_4OH$ | All in $NH_4OH$ | 71.00 | 57.00 | 2 |
| 13 | 0.75 | All $NH_4OH$ | ½ in $NH_4OH$ ½ in BM | 96.78 | 79.00 | 3 |
| 14 | 0.88 | All $NH_4OH$ | ¾ in $NH_4OH$ ¼ in BM | 97.11 | 79.00 | 2 |
| 15 | 0.72 | All $NH_4OH$ | ¼ in $NH_4OH$ ¾ in BM | 88.31 | 75.37 | 2 |
| 16(b) | 0.3 | All $NH_4OH$ | 2.3 g water per g BM | 83.58 | 68.18 | 1 |
| 17(b) | 0.15 | All $NH_4OH$ | 5.6 g water per g BM | 70.50 | 42.46 | 1 |
| 18(b) | 0.1 | All $NH_4OH$ | 9 g water per g BM | 64.85 | 49.31 | 1 |
| 19(b) | 0.05 | All $NH_4OH$ | 19 g water per g BM | 51.26 | 39.32 | 1 |
| 20(c) | Control | No ammonia | Not applicable | 29.5 | 17.5 | 2 |

Note:
Pressures range from about 100 psia to about 300 psia except for Expt. 16-19, which are at atmospheric pressure
(a)Comparative Example 1 shows the AFEX process described in U.S. Pat. Nos. 4,600,590 and 5,037,663 to Date, exemplified by FIG. 1. Comparative Examples 16 to 19
(b)show the results at atmospheric pressure with ammonium hydroxide Example 20
(c)shows the process without ammonia.

Table 1 shows the results for the conversion of corn stover to glucose and xylose following treatment with ammonia and water. The total amount of water, ammonia and biomass and the system temperature is the same in all cases. The biomass was treated with 1 kg of ammonia per 1 kg dry biomass (the untreated stover has a moisture content of about 15% dry basis). The experiments were run at 90° C. with a five minute holding time at that temperature and the treated material of Example 1 was hydrolyzed with 15 filter paper units of cellulose per gram of cellulose in the stover. From the point of view of the final conditions to which the stover was subjected, these conditions are identical.

The first two (2) columns of the Table show how this was done. For example, the column titled "Ammonia Addition" shows whether the ammonia (as NH3) was added as anhydrous ammonia or as ammonium hydroxide (ammonia in water). For example, "all NH3" means that all of the ammonia was added to the biomass as anhydrous liquid ammonia has in Example directly from the pressure tank. "ALL NH4OH" means all of the ammonia was added as aqueous ammonium hydroxide.

The second column shows whether the water was added to the stover directly or added as part of the ammonium hydroxide. In the first row, "all $NH_3$" and "All of the water in EM" means that all the ammonia was added as anhydrous and all of the water was in the biomass as in Example 1. The last set of rows is for "All $NH_4OH$" meaning that ail of the ammonia was added as ammonium hydroxide and the water was added either to the stover or with the ammonium hydroxide.

Thus, depending on how the ammonia and water are added, very different results are obtained. Eighty-five percent (85%) conversion of cellulose to glucose is used as the minimum for a cost competitive process. Using that criterion, the final column shows the % yield after 168 hours of hydrolysis for both glucose (G) and xylose (X). In no case, when all of the water was added as ammonium hydroxide (comparatively more dilute ammonium hydroxide) is the 85% criterion achieved.

It appears from Table 1 that the ammonium concentration is important. Water naturally associated with the biomass does not act as free water available to dilute the ammonia.

The specific features of the process of the present invention that make it more advantageous than prior art methods are as follows: (1) it does not degrade any biomass carbohydrates so that yield is not compromised due to the pretreatment; (2) high overall yields of glucose (nearly 100% of theoretical) and 85% of theoretical yields of xylose, are obtained; (3) low application rates of otherwise expensive hydrolytic enzymes are needed to obtain these yields; (4) residual ammonia can serve as a nitrogen source for subsequent fermentations or animal feeding operations; (5) treated biomass and polysaccharides can be fed at very high solids levels to subsequent process operations, thereby increasing the concentration of all products and reducing the expense of producing other chemicals from the polysaccharides; and (6) using ammonia and ammonium hydroxide combinations fits well into recovery operations for the ammonia.

Markets that can use this invention include: (1) the U.S. chemical industry which is beginning to move away from petroleum as a source of chemical feedstocks and is interested in inexpensive monosaccharides as platform chemicals for new, sustainable processes; (2) the fermentation industry, especially the fuel ethanol production industry which is also interested in inexpensive sugars from plant biomass; and (3) the animal feed industry which is strongly affected by the cost of available carbohydrates/calories for making animal feeds of various kinds.

The following Example 16 describes two (2) design features that reduce process energy requirements relative to existing designs of ammonia recovery for AFEX pretreatment: (1) steam stripping of pretreated material; and (2) water quench condensation of ammonia vapor. FIG. 2 presents a process flow sheet of these features in the context of the broader AFEX pretreatment design.

Steam Stripping of Pretreated Material

After the AFEX pretreatment is complete, the pretreated material is flashed to a lower pressure, as in the existing design. Unlike the existing design; however, the present invention uses steam-stripping of the resulting pretreated solids to recover residual ammonia. This feature enables the elimination of energy intensive solids drying that is used in the design of FIG. 1. The processing equipment can be similar to that used for direct steam drying of solids for which there are an increasing number of commercial examples (Kudra, T., A. S. Mujumdar, 2002. Advanced Drying Technologies, New York, N.Y.: Marcel Dekker, Inc.; Pronyk, C., S. Cenkowski, 2003. "Superheating Steam Drying Technologies," ASAE Meeting Presentation, Paper Number RRV03-0014.).

Water Quench Condensation of Ammonia Vapor

Ammonia vapor coming from the ammonia recovery steam stripping column is combined with ammonia vapor arising from the post-AFEX flash operation and condensed by first adding water in the mixer and then indirectly cooling the aqueous solution in two steps, first with cooling water, and then with chilled water. The condensed aqueous mixture is then pressurized via liquid pumping and recycled to the AFEX reactor. These steps eliminate the need for ammonia vapor compression that is used in the design of FIG. 1.

Utility of Invention

Based on Aspen Plus (a commercially available modeling software) process simulations of the process of FIGS. 1 and 2, the present invention requires significantly less process energy relative to the existing design, as indicated in Table 2. Furthermore, it is anticipated that the invention will result in lower processing costs as well.

TABLE 2

Comparison of process energy requirements: proposed versus existing design for AFEX pretreatment with ammonia recovery.[1,2]

| | FIG. 1 Design Required Energy | FIG. 2 Design Required Energy |
|---|---|---|
| Energy Flow | % feedstock LHV) | (% feedstock LHV) |
| Steam to dryer | 7.73% | — |
| Steam to $NH_3$ column | 2.87% | 3.82% |
| Power to compressor | 0.02% | — |
| Power to chilled water unit | — | 0.14% |
| Total | 10.62% | 3.96% |

[1]Energy necessary to achieve AFEX reaction temperature is met entirely by heat of mixing between ammonia and water in the reactor.
[2]Both designs use the same ammonia and water loadings: 0.3 g $NH_3$/g biomass; 0.5 g $H_2O$/g biomass.

While the present invention is described herein with reference to illustrated embodiments, it should be understood that the invention is not limited hereto. Those having ordinary skill in-the art and access to the teachings herein will recognize additional modifications and embodiments within the scope thereof. Therefore, the present invention is limited only by the claims attached herein.

What is claimed is:

1. A process for treating lignocellulosic biomass containing structural carbohydrates comprising:
   adding ammonia vapors and water vapors at an elevated temperature to a closed vessel containing dry lignocellulosic biomass such that structural carbohydrates in the dry lignocellulosic biomass are rendered more susceptible to hydrolysis, wherein the ammonia vapors and the water vapors are added at an elevated pressure.

2. The process of claim 1 wherein a final mixture temperature in the closed vessel is 50° C. or above.

3. The process of claim 2 wherein the final mixing temperature is about 90° C.

4. The process of claim 1 wherein a ratio of ammonia in the ammonia vapors to the dry lignocellulosic biomass is from about 0.2:1 to about 1:1.

5. The process of claim 4 wherein a weight ratio of water in the water vapors to the dry lignocellulosic biomass is from about 0.4:1 and to about 1:1.

6. The process of claim 1 wherein the elevated pressure is released.

7. The process of claim 1 wherein a weight ratio of water in the water vapors to the dry lignocellulosic biomass is between about 0.4:1 and about 1:1.

8. The process of claim 1 wherein the elevated temperature is a temperature of a mixture of ammonia, biomass and water.

9. The process of claim 8 wherein the elevated temperature is between about 50° C. and 120° C.

10. The process of claim 9 wherein the elevated pressure is between about 4 and about 50 atm.

11. The process of claim 10 wherein the elevated pressure is between about 6.9 and 20.7 atm.

12. The process of claim 1 wherein the dry lignocellulosic biomass is ground dry lignocellulosic biomass.

13. The process of claim 1 further comprising obtaining monosaccharides from the treated dry lignocellulosic biomass.

14. The process of claim 13 wherein the monosaccharides are obtained by enzymatic hydrolysis, microbial conversion and/or animal digestion.

15. The process of claim 13 wherein the monosaccharides are recovered as a mixture of glucose, xylose, arabinose and other sugars.

16. The process of claim 14 wherein the enzymatic hydrolysis is performed with a cellulase enzyme.

17. The process of claim 14 wherein the microbial conversion produces organic acids, alcohols, and other byproducts.

18. The process of claim 14 wherein the animal digestion occurs in either ruminant or non-ruminant animal diets.

19. The process of claim 1 wherein the pressure is released rapidly.

20. A process comprising:
adding ammonia vapors and water vapors at an elevated temperature to a closed vessel containing dry plant biomass to produce pretreated dry plant biomass, wherein structural carbohydrates present in the dry plant biomass are rendered more susceptible to hydrolysis, and a weight ratio of water in the water vapors to the dry plant biomass is between about 0.4:1 and about 1:1.

21. The process of claim 20 wherein the method further comprises adding the ammonia vapors and the water vapors at an elevated pressure.

22. The process of claim 21 wherein the elevated pressure is between about 4 and about 50 atm.

23. The process of claim 21 wherein the elevated pressure is released.

24. The process of claim 20 wherein a ratio of ammonia in the ammonia vapors to the dry plant biomass is from about 0.2:1 to about 1:1.

25. The process of claim 20 wherein the dry plant biomass is corn stover or switchgrass.

\* \* \* \* \*

UNITED STATES PATENT AND TRADEMARK OFFICE
CERTIFICATE OF CORRECTION

PATENT NO. : 8,771,425 B2  
APPLICATION NO. : 13/591092  
DATED : July 8, 2014  
INVENTOR(S) : Bruce E. Dale Page 1 of 1

It is certified that error appears in the above-identified patent and that said Letters Patent is hereby corrected as shown below:

On the Title Page, Item (56) References Cited  
Page 4/Other Publications: Error reads as "Appied" and should read as "Applied"

In the Specification  
Pat. Col. 5/Line 3: Error reads as "Typically this" and should read as "Typically, this"  
Pat. Col. 5/Line 4: Error reads as "In general this" and should read as "In general, this"  
Pat. Col. 5/Line 5: Error reads as "biomass and thus" and should read as "biomass. Thus"  
Pat. Col. 5/Line 38: Error reads as "and condenser" and should read as "and condensed"

Pat. Col. 6/Line 3 (Table 1/Line 2): Error reads as "cellulose" and should read as "cellulase"  
Pat. Col. 6/Line 5 (Table 1/Line 3): Error reads as "NH3" and should read as "$NH_3$"  
Pat. Col. 6/Line 57 (Table 1/Note (a)/Line 2): Error reads as "Date" and should read as "Dale"

Pat. Col. 7/Line 5: Error reads as "the Table" and should read as "Table 1"  
Pat. Col. 7/Line 7: Error reads as "(as NH3)" and should read as "(as $NH_3$)"  
Pat. Col. 7/Line 9: Error reads as "For example, "all NH3" means" and should read as "For example, "all $NH_3$" means"  
Pat. Col. 7/Lines 10-11: Error reads as "ammonia has in Example directly from the pressure tank. "ALL NH4OH" means" and should read as "ammonia (as in Example 1) directly from the pressure tank. "ALL $NH_4OH$" means"  
Pat. Col. 7/Line 19: Error reads as "ail" and should read as "all"

Signed and Sealed this  
Fourteenth Day of October, 2014

Michelle K. Lee  
*Deputy Director of the United States Patent and Trademark Office*

UNITED STATES PATENT AND TRADEMARK OFFICE
CERTIFICATE OF CORRECTION

PATENT NO. : 8,771,425 B2  
APPLICATION NO. : 13/591092  
DATED : July 8, 2014  
INVENTOR(S) : Bruce E. Dale It is certified that error appears in the above-identified patent and that said Letters Patent is hereby corrected as shown below:

Title Page, Item (63) U.S. Related Application Data "PCT/US2007/010454" should read as "PCT/US2007/010415"

In the Specification

Col. 1/Lines 10-11: "PCT/US2007/010454" should read as "PCT/US2007/010415"

Signed and Sealed this
Twenty-second Day of March, 2016

Michelle K. Lee
*Director of the United States Patent and Trademark Office*